United States Patent [19]

Morhenn

[11] 4,031,886
[45] June 28, 1977

[54] OCCLUSIVE PESSARY

[76] Inventor: Vera B. Morhenn, 731 De Soto, Palo Alto, Calif. 94303

[22] Filed: Aug. 30, 1976

[21] Appl. No.: 718,614

Related U.S. Application Data

[63] Continuation of Ser. No. 612,284, Sept. 11, 1975, abandoned.

[52] U.S. Cl. .............................................. 128/130
[51] Int. Cl.² ............................................ A61F 5/24
[58] Field of Search ................. 128/127, 130, 131

[56] References Cited

UNITED STATES PATENTS 1,552,878  9/1925  Potter .............................. 128/127
3,545,439  12/1970  Duncan ............................ 128/130

Primary Examiner—Louis G. Mancene
Assistant Examiner—Robert F. Cutting
Attorney, Agent, or Firm—Phillips, Moore, Weissenberger, Lempio & Majestic

[57] ABSTRACT

A pessary is described which not only serves to support and protect the position of the uterus but is also occlusive in order to enable the local application of medication and to achieve contraception. The specific shape of the pessary in order to provide ease in handling and application is disclosed. Embodiments preferred for hygienic reasons and for the timed application of medications are described.

13 Claims, 4 Drawing Figures

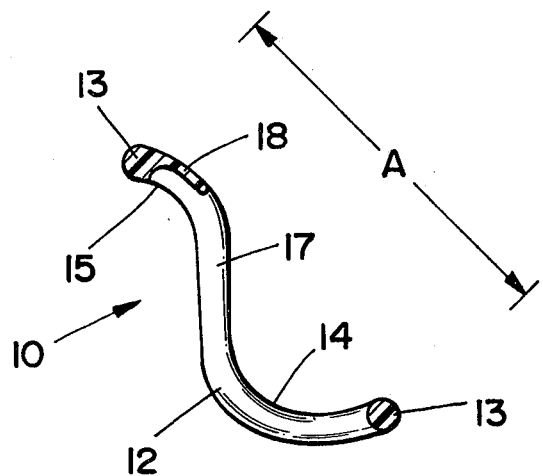
FIG_2
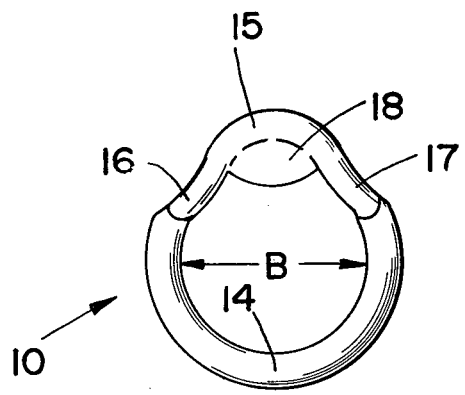
FIG_3
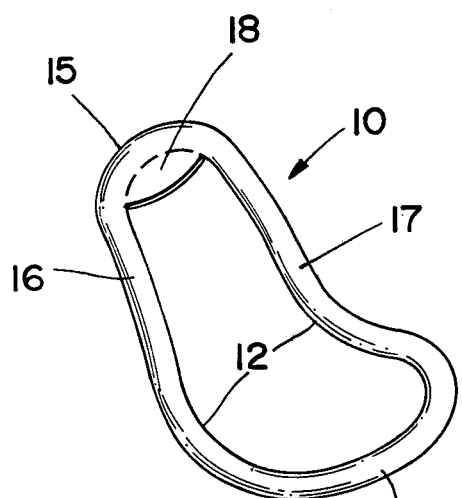
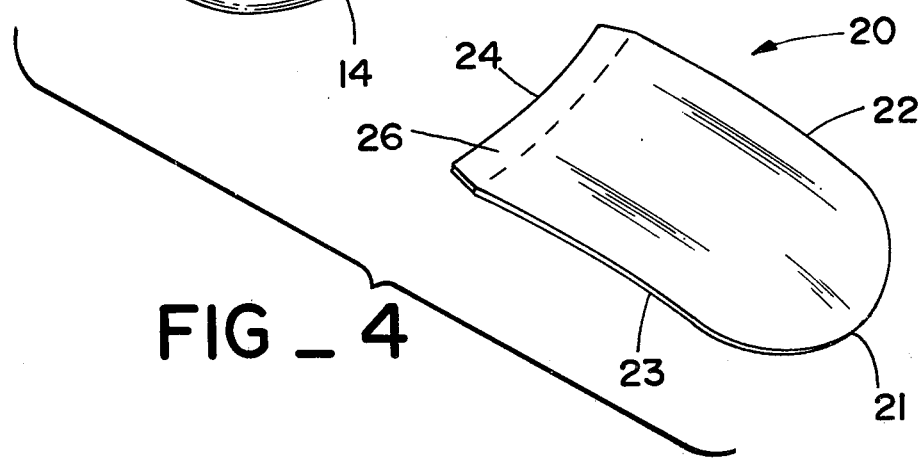
FIG_1
FIG_4

OCCLUSIVE PESSARY

This is a continuation of Serial No. 612,284, filed Sept. 11, 1975, now abandoned.

BACKGROUND OF THE INVENTION

As is commonly known in the art, the word "pessary" describes a medical instrument which is placed into the vagina in order to support the uterus and stabilize its position. Conventional pessaries comprise a member of circular cross-section formed into a closed figure of generally oval shape. Such pessaries are generally tailored to the anatomy of each individual patient by a physician and may be made occlusive by the provision of a diaphragm across one side of the generally oval figure.

Due to the minimal and at best only linear contact of the pessary about the uterus, the necessary uterine support and stabilization are not often achieved. This is particularly true since hygienic reasons necessitate periodic removal of the pessary and even though the patient has been instructed by her physician with respect to the insertion and removal of the pessary, it is necessary for the patient to develop a certain dexterity in order to be able to insert the device into its proper therapeutically effective position. Even where the pessary is formed molding directly from the cervix uteri of the actual wearer, as taught in British Pat. No. 5028 and to remain during wear by adhesion, it is often misplaced by the wearer and in any event presents great difficulties in insertion and removal without the assistance of a physician.

The teaching of German Pat. No. 818,078 represents a substantial improvement in the art particularly with regard to ease the handling and proper positioning of the pessary by the wearer without the assistance of a physician each time the pessary is removed and subsequently reinserted for hygienic reasons. This is due to the fact that the pessary according to the teaching of the German patent is a continuous surface having a cross-section which approximates the form of an "S", one end of the "S"-form serving as a handle and the other end as a bowl in the manner of a dipper. The bowl-shaped end not only encompasses the uterine cervix but can also serve as a receptacle for various medications. The "S" form is peculiarly adaptable to the pear-shaped uterus providing a large amount of surface contact between such form and thus increased support since the pessary conforms to the anatomic structure of the vagina at the cervico-vaginal junction. The handle portion of the pessary increases uterine stablization and facilitates the removal and reinsertion of the pessary into its correct position after cleansing by the patient.

However, according to the teaching of German Pat. No. 818,078, the pessary was made of a thermo-plastic material and was molded to fit the individual anatomic structure of each patient by a physician. Thus, although the pessary was much easier to handle, such individual fitting again created problems with respect to the proper positioning thereof by the patient upon reinsertion and of course, the initial fitting or tailoring of the device to the individual was expensive, time-consuming and uncomfortable to the patient.

It is an object of this invention to provide a pessary which is easy for the wearer to remove and reinsert and which will provide proper support for the cervix without undue requirements as to positioning thereof.

It is another object of this invention to provide a pessary which when made in a number of different sizes will accommodate the anatomical variations in the cervico-vaginal structure among substantially all individuals without fitting or tailoring by a physician to specific individuals.

It is yet another object of this invention to provide a pessary having improved hygienic features and which provides for the timed release of medicaments in use.

SUMMARY OF THE INVENTION

Briefly, a pessary for the support and stabilization of the human uterus according to this invention comprises a frame made of an elongated body of generally circular cross-support formed into a closed figure of generally oval shape. In side view the frame is of generally "S" shape providing a first semicircular portion in a given plane at one end thereof for receiving the human cervix at the cervico-vaginal junction. The frame also provides a pair of arms curving away from the given plane of the first semicircular portion to an angle substantially normal to such plane and merging together at the other end of the frame in a second semicircular portion extending in a plane at a small angle to the given plane of the first semicircular portion. According to this invention, the pessary may be used in combination with a bag comprising two generally planar walls each having four edges, which walls are joined to each other along three of their edges, at least the first semicircular portion of said frame being received within the bag with a snug fit whereby said pessary may be made occlusive and medicaments may be applied to the cervix received therein.

BRIEF DESCRIPTION OF THE DRAWING

The foregoing and other objects and features of the subject invention will be more fully understood from the following detailed description of a preferred embodiment thereof as shown in the drawing wherein:

FIG. 1 is a perspective view of a pessary in accordance with the teaching of this invention, as assembled with a bag in accordance with the teaching of this invention, for use.

FIG. 2 is a side view in cross-section of the pessary of FIG. 1.

FIG. 3 is a top view in elevation of the pessary of FIG. 1.

FIG. 4 is an exploded view in perspective of the pessary and bag of FIG. 1 prior to assembly thereof.

DETAILED DESCRIPTION OF PREFERRED EMBODIMENT

Referring to FIG. 1, a pessary 10 according to the teaching of this invention is shown in perspective as received within a bag 20 according to the teaching of this invention. The bag 20 may be transparent, as shown in FIG. 1, although it may also be opaque due to the impregnation thereof with medicaments as will be more fully discussed hereinafter. In any event, the walls of the bag 20 are very thin and flexible and may be made of resilient material.

As shown in FIGS. 1 and 4, the pessary 10 according to this invention comprises an elongated body 12 formed into a closed figure of generally oval shape in perspective. Such closed figure is smoothly curved in order to provide the desired shape without producing points of stress concentration which could be irritating during extended periods of contact with the human anatomy.

Similarly, as best shown in FIG. 2, the elongated body 12 has a circular cross-section 14 in order to distribute the stress of the contact between the pessary and the human anatomy over the surface thereof. As is also best shown in FIG. 2, the pessary has a generally "S"-shape in side view providing a first semicircular portion 14 extending in a given plane at one end thereof and a second semicircular portion 15 at the other end thereof extending in a plane at a small angle to the plane of the first semicircular portion 14 with a pair of arms 16 and 17 extending generally normal to the planes of the semicircular portions 14 and 15 and smoothly joining said portions together into the closed figure as shown in FIGS. 1 and 4.

The semicircular portions 14 and 15 are best shown in FIG. 3 which is a top view of the pessary 10 according to the preferred embodiment of this invention. As shown in FIG. 3 the first semicircular portion 14 of the pessary 10 has a larger radius of curvature than the second semicircular portion 15 of the pessary 10. In addition, the first semicircular portion 14 of the pessary 10 defines somewhat more than 180° of a circle whereas the second semicircular portion 15 of the pessary 10 may define somewhat less than 180° of a circle.

As shown in FIG. 3, the first semicircular portion 14 of the pessary 10 extends in the plane of the site of the figure, whereas the second semicircular portion 15 lies in a plane extending at a slightly upward angle from the plane of the site of the figure.

As best shown in FIGS. 2 and 3, the second semicircular portion 15 of the pessary 10 may be provided with an integrally formed web or wall 18 extending thereacross. Thus, the first semicircular portion 14 of the pessary 10 is dimensioned to receive the cervix of the wearer thereof and the second semicircular portion 15 of the pessary together with the arms 16 and 17 provides a handle which will facilitate the insertion and removal of the pessary 10. The web or wall 18 of the second semicircular portion 15 of the pessary and its circular cross-section cooperate to provide a grip for the finger or fingernail of the wearer during the insertion and removal of the pessary 10. In addition, the web or wall 18 provides a smoothly curved pressure surface for contact with the vaginal wall to hold the pessary 10 firmly in place during use without exerting excessive pressure on such vaginal wall.

A pessary 10 according to the teaching of this invention having a length as indicated by the arrow A in FIG. 2 between about 4.5 cm and about 9 cm and a first semicircular portion having a diameter indicated the arrow B in FIG. 3 between about 4.5 cm and about 8.0 cm will provide the desired support and positioning of the cervix of substantially all individuals. Thus, it is proposed to manufacture the pessary according to the teaching of this invention in a number of different sizes such as three, for example, the first of which would have the smallest length A and diameter B of the above ranges, the second of which would have the largest length A and diameter B of the above ranges and the third of which would have an intermediate length A and diameter B. Additional sizes combining lengths A and diameters B within the above ranges as appropriate, could be added as necessary and desirable.

The pessary 10 may be made of an appropriate plastic or comparatively rigid rubber. Appropriate mass production techniques may be used for making the various sizes of the pessary 10 as found necessary and desirable.

For each size of pessary 10 an appropriate insert or bag 20 made of rubber or plastic film as best shown in FIG. 4 may be provided. The bag 20 may, for example, comprise two walls each having four edges 21, 22, 23 and 24 with three of the edges 21, 22 and 23 of the walls joined together. The walls of the bag 20 are dimensioned to allow the pessary 10 to be received therebetween. The fit of the pessary 10 within the bag 20 should be fairly snug. However, it is desirable that the insert or bag 20 form a loose pouch or sack at the inner end thereof which receives the first semicircular portion 14 of the pessary 10. This will provide a loose pouch or sack which will insure a large surface area for contact with the cervix. Thus, the insert or bag 20 provides an occlusive feature for the pessary 10 for the protection of the cervix. In addition, the insert or bag 20 provides for the treatment of the cervix with medicaments of various kinds and since they are disposable and may receive the entire pessary therein, they provide a hygienic feature for maintaining the cleanliness of the pessary 10 for repeated use.

The occlusive insert or bag 20 may be impregnated with either spermicidal agents to provide contraception or with medicaments such as progesterone or prostaglandines which are most effectively applied locally for therapeutic reasons. In addition, the insert or bag 20 could be made of a plastic film previous to the desired drug and a quantity of the desired drug placed within the bag 20 for timed release thereof through the walls of the bag 20.

In actual use, a physician would initially fit the patient with a pessary of the size most suitable for her anatomic structure. The increased surface contact between the pessary and the uterus will increase support and better positioning due to the fact that it conforms to the anatomic structure of the vagina at the cervico-vaginal junction. Furthermore, the structure of the pessary, according to the teaching of this invention, will facilitate removal and reinsertion of the pessary into its correct and most effective position after removal by the user for hygienic purposes or to replenish the medicaments involved in its use.

It is believed that those skilled in the art will make obvious changes and adaptations of the pessary according to the teaching of this invention for specific purposes. In particular, the number of sizes and the specific interrelation of the dimensions of the pessary according to this invention are subject to variation within the broad ranges given hereinabove. The insert or bag 20 may be made in various ways to provide the occlusive and medicament dispensing features dicussed hereinabove. For example, the inner end of the bag 20 may be curved to fit the shape of the pessary 10 and may be slightly enlarged to enhance the amount of slack present at such inner end for the formation of a bowl or receptacle for receiving the end of the cervix as well as the medicaments to be applied thereto. Similarly, the open end of the insert or bag 20 may be provided with a self-adhesive inner portion 26 in order to provide for the sealing of the bag and its firm attachment to the pessary 10 in use.

What is claimed is:

1. A pessary for the support and stabilization of the human uterus comprising a frame made of an elongated body of generally circular cross-section formed into a closed figure of generally oval shape, said frame being of generally "S" shape in side view providing a first semicircular portion in a given plane at one end for receiving the human cervix at the cervico-vaginal junction, a pair of arms curving away from said given plane of said first semicircular portion to an angle substantially normal thereto and merging together at the other end of said frame in a second semicircular portion extending in a plane at a small angle to said given plane.

2. A pessary as claimed in claim 1 wherein said second semicircular portion has a smaller radius than said first semicircular portion.

3. A pessary as claimed in claim 2 wherein said first semicircular portion defines more than 180° of a circle and said second semicircular portion defines less than 180° of a circle.

4. A pessary as claimed in claim 1 wherein said second semicircular portion includes a wall formed integrally with said elongated member of circular cross-section and extending across said second semicircular portion at the side thereof remote from said first semicircular portion.

5. A pessary as claimed in claim 2 wherein said generally "S" shape of said frame has a maximum length from said one end to said other end thereof of between about 4.5 cm and about 9.0 cm and said first semicircular portion has a diameter between about 4.5 cm and about 8.0 cm with said length and said diameter being in general correspondence with each other.

6. In combination a pessary as claimed in claim 1 and a bag comprising two generally planar walls each having four edges, said walls joined to each other along three of said edges and at least said first semicircular portion at said one end of said pessary being received within said bag.

7. The combination claimed in claim 6 wherein substantially said entire pessary is received within said bag, said walls of said bag including a self-adhesive internal portion at the unjoined edges thereof.

8. The combination claimed in claim 7 wherein the portion of said bag receiving said semicircular portion at said one end of said frame is oversized to provide sufficient slack to form a bowl-like receptacle at said one end thereof.

9. The combination claimed in claim 6 wherein said walls of said bag are impregnated with medicaments and provide timed release thereof.

10. The combination claimed in claim 6 wherein said bag contains a quantity of a medicament and said walls of said bag are pervious to said medicament for timed release thereof.

11. A occlusive pessary for the support and stabilization of the human uterus comprising a frame made of an elongated body of generally circular cross-section formed into a closed figure of generally oval shape, said frame being of generally "S" shape in side view providing a first semicircular portion in a given plane at one end for receiving the human cervix at the cervico-vaginal junction, a pair of arms curving away from said given plane of said first semicircular portion to an angle substantially normal thereto and merging together at the other end of said frame in a second semicircular portion extending in a plane at a small angle to said given plane; and a wall of thin and flexible material mounted on said frame, said wall being of generally oval shape coextensive with said closed figure of generally oval shape and having its boundaries in engagement with said elongated body forming said closed figure generally oval shape.

12. An occlusive pessary as claimed in claim 11 wherein said wall of thin and flexible material is provided by a bag receiving therewithin said closed figure of generally oval shape formed by said elongated body.

13. In combination, a pessary for the support and stabilization of the human uterus comprising a frame made of an elongated body of generally cross-section formed into a closed figure; and a bag made of thin and flexible material receiving said frame entirely therewithin, whereby said frame is totally enclosed within said bag.

* * * * *

UNITED STATES PATENT OFFICE
CERTIFICATE OF CORRECTION

Patent No. 4,031,886   Dated June 28, 1977

Inventor(s) VERA B. MORHENN

It is certified that error appears in the above-identified patent and that said Letters Patent are hereby corrected as shown below:

Column 2, line 15, "cross-support" should read --cross-section--.
Column 6, line 28, after "figure" --of-- has been omitted.
Column 6, line 35, after "generally" --circular-- should be inserted.

Signed and Sealed this

Thirtieth Day of October 1979

[SEAL]

Attest:

RUTH C. MASON
Attesting Officer

LUTRELLE F. PARKER
Acting Commissioner of Patents and Trademarks